(12) United States Patent
Kawamura

(10) Patent No.: US 12,167,681 B2
(45) Date of Patent: Dec. 10, 2024

(54) ANTHRACENE DERIVATIVES AND ORGANIC ELECTRONIC DEVICE USING SAME

(71) Applicant: LG Chem, Ltd., Seoul (KR)

(72) Inventor: Hisayuki Kawamura, Tokyo (JP)

(73) Assignee: LG Chem, Ltd., Seoul (KR)

( * ) Notice: Subject to any disclaimer, the term of this patent is extended or adjusted under 35 U.S.C. 154(b) by 754 days.

(21) Appl. No.: 17/296,032

(22) PCT Filed: Feb. 14, 2020

(86) PCT No.: PCT/KR2020/002087
§ 371 (c)(1),
(2) Date: May 21, 2021

(87) PCT Pub. No.: WO2020/171480
PCT Pub. Date: Aug. 27, 2020

(65) Prior Publication Data
US 2022/0013728 A1 Jan. 13, 2022

(30) Foreign Application Priority Data
Feb. 20, 2019 (JP) ................ 2019-028321

(51) Int. Cl.
H10K 85/60 (2023.01)
C07D 307/91 (2006.01)
H10K 50/11 (2023.01)

(52) U.S. Cl.
CPC ......... *H10K 85/615* (2023.02); *C07D 307/91* (2013.01); *H10K 85/6574* (2023.02); *H10K 50/11* (2023.02)

(58) Field of Classification Search
CPC .................................. H10K 85/615
USPC ...................................... 549/460
See application file for complete search history.

(56) References Cited

U.S. PATENT DOCUMENTS

| | | | |
|---|---|---|---|
| 5,935,721 A | 8/1999 | Shi et al. | |
| 2007/0106103 A1 | 5/2007 | Ikeda et al. | |
| 2007/0247063 A1 | 10/2007 | Murase et al. | |
| 2010/0314615 A1 | 12/2010 | Mizuki et al. | |
| 2013/0048955 A1 | 2/2013 | Lee et al. | |
| 2013/0299798 A1 | 11/2013 | Seo et al. | |
| 2014/0183485 A1 | 7/2014 | Yoon et al. | |
| 2017/0018723 A1 | 1/2017 | Cha et al. | |
| 2018/0233669 A1 | 8/2018 | Lee et al. | |
| 2018/0277771 A1 | 9/2018 | Park et al. | |
| 2018/0351101 A1 | 12/2018 | Suruga et al. | |
| 2019/0088897 A1 | 3/2019 | Seo et al. | |
| 2019/0296243 A1 | 9/2019 | Suh et al. | |
| 2020/0052212 A1 | 2/2020 | Tasaki et al. | |
| 2020/0131124 A1 | 4/2020 | Suh et al. | |
| 2021/0217963 A1 | 7/2021 | Choi et al. | |

FOREIGN PATENT DOCUMENTS

| | | |
|---|---|---|
| CN | 102449110 A | 5/2012 |
| EP | 3333241 A1 | 6/2018 |
| EP | 3767695 A1 | 1/2021 |
| JP | 2012522041 A | 9/2012 |
| JP | 2013043889 A | 3/2013 |
| JP | 2017199913 A | 11/2017 |
| JP | 2017199914 A | 11/2017 |
| KP | 20180131963 A | 12/2018 |
| KR | 20100109293 A | 10/2010 |
| KR | 20130075982 A | 7/2013 |
| KR | 20140085045 A | 7/2014 |
| KR | 20170009714 A | 1/2017 |
| KR | 20170044001 A | 4/2017 |
| KR | 20170096860 A | 8/2017 |
| KR | 20170116885 A | 10/2017 |
| KR | 20180027676 A | 3/2018 |
| KR | 20180071850 A | 6/2018 |
| KR | 20180084909 A | 7/2018 |
| KR | 20190013605 A | 2/2019 |
| KR | 102250389 B1 | 5/2021 |
| WO | 2005056505 A1 | 6/2005 |
| WO | 2005113531 A1 | 12/2005 |
| WO | 2009084512 A1 | 7/2009 |
| WO | 2010010924 A1 | 1/2010 |

(Continued)

OTHER PUBLICATIONS

King, Med. Chem, Principle and Practice (1994) 206-208.*
Extended European Search Report for Application No. 20759249.4 dated Dec. 2, 2021, pp. 1-3.
Zhiqiang, W. et al., "Synthesis and Characterization of Blue Light Host Materials for Organic Small Molecule Electroluminescent Devices" Chemical Journal of Chinese Universities, Jilin University and Nankai University, Nov. 2007, 1 page.
Xiang, L.et al., "Top-emitting organic light-emitting devices with microcavity structure based on Alq3 and anthracene derivative material" Journal of Functional Materials and Devices, Department of Material, Shanghai University, Shanghai 200072, China, Oct. 2007, 1 page.

(Continued)

*Primary Examiner* — Taofiq A Solola
(74) *Attorney, Agent, or Firm* — Lerner David LLP

(57) ABSTRACT

An object of the present invention is to provide a novel compound represented by the following Formula 1 that is useful as a material for an organic electronic device, particularly, an organic EL device, particularly as a light emitting material, and an organic electronic device using the same, particularly, an organic EL device:

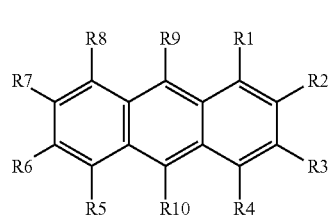

[Formula 1]

wherein R1 to R10 are described herein.

11 Claims, 1 Drawing Sheet

(56) References Cited

FOREIGN PATENT DOCUMENTS

| WO | 2010114253 A2 | 10/2010 |
| WO | 2015174682 A1 | 11/2015 |
| WO | 2018117369 A1 | 6/2018 |
| WO | 2018164510 A1 | 9/2018 |
| WO | 2018186404 A1 | 10/2018 |
| WO | 2019022562 A1 | 1/2019 |

OTHER PUBLICATIONS

Jianfeng, L. et al., "Synthesis of the 9,9'-bianthracene and fabrication of white organic light emitting devices" Journal of Functional Materials, Lanzhou University, School of Physical Science and Technology, Jun. 2009, 1 page.

International Search Report for Application No. PCT/KR2020/002087, mailing May 22, 2020, 7 pages.

* cited by examiner

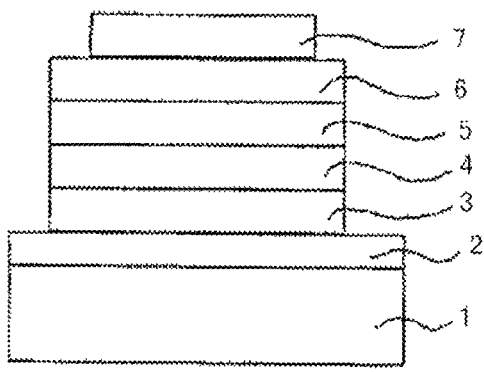

ANTHRACENE DERIVATIVES AND ORGANIC ELECTRONIC DEVICE USING SAME

CROSS-REFERENCE TO RELATED APPLICATION(S)

This present application is a national phase entry under 35 U.S.C. § 371 of International Application No. PCT/KR2020/002087 filed Feb. 14, 2020, which claims priority from Japanese Patent Application No. 2019-028321 filed Feb. 20, 2019, all of which are incorporated herein by reference in their entirety.

TECHNICAL FIELD

The present invention relates to an anthracene derivative, and an organic electronic device using the same, for example, an organic solar cell, an organic photo conductor (OPC), and an organic light emitting device, and more particularly, to an organic electroluminescence (EL) device, an organic transistor, particularly, an organic light emitting device, and an organic EL device among them.

The anthracene derivative of the present invention is particularly useful as a light emitting material for an organic EL device.

BACKGROUND ART

An organic electronic device is an element that requires the transport of charges between an electrode and an organic material layer which constitute the device, using holes and/or electrons. The organic electronic device may be roughly divided into two types of electronic devices as follows, depending on the operation principle.

The first type of device is an electronic device in which excitons are formed in an organic material layer by photons incident to the device from an external light source, the excitons are separated into electrons and holes, and the electromotive force generated by the transport of the electrons and holes to separate electrodes, respectively is used. The second type of device is an electronic device in which holes and/or electrons are injected into an organic material semiconductor layer brought into contact with each electrode by applying a voltage to two or more separate electrodes or flowing current to the device, and the device is operated by the injected electrons and holes. Examples of the first type of device include an organic solar cell and an organic photo conductor (OPC). Examples of the second type of device include an organic light emitting device, more specifically, an organic electroluminescence (EL) device, and an organic transistor.

Among the organic electronic devices, the organic EL device typically has a structure including an anode and a cathode, and an organic material layer disposed between these electrodes and including an emission layer. In the organic EL device, light is emitted from a light emitting material using the energy of the exciton generated by the recombination of holes and electrons injected from the anode and the cathode, respectively. Here, generally, an organic material layer of the organic EL device has a multi-layer structure consisting of a plurality of layers including different materials having different functions in order to enhance characteristics of the organic EL device, for example, the light emitting efficiency, and the plurality of layers are composed of, for example, a hole injection layer, a hole transport layer, an emission layer, an electron transport layer, an electron injection layer, and the like. However, one layer may be responsible for several functions of these layers, and accordingly, several of these layers may be omitted. Further, in addition to these organic material layers, a planarization layer for enhancing the smoothness of the surface of an electrode, and a hole blocking layer, an electron blocking layer, and/or a hole blocking layer for confining holes, electrons, and/or excitons in an emission layer may be included in an organic layer of the organic EL device.

In an organic EL device having such a structure, when a voltage is applied between two electrodes, holes and electrons are injected from an anode and a cathode, respectively, into an organic material layer, and when the injected holes and electrons are combined, excitons having higher energy than the ground state energy of a luminescent molecule are formed in the luminescent molecule, and light is emitted when the excitons are returned to the ground state. Such an organic EL device is a self-luminous light emitting device, and is known to have characteristics such as high brightness, high efficiency, a low driving voltage, a wide viewing angle, high contrast, and a high speed response as compared to a liquid crystal device using a backlight in the related art.

A light emitting material used in the organic EL device may be classified into blue, green, and red light emitting materials according to the light emitting color, and yellow and orange light emitting materials required to realize a better natural color. Further, when an emission layer is formed with only one material, there may occur problems in that the maximum light emitting wavelength moves to a longer wavelength, and thus the color purity deteriorates due to the intermolecular interaction, or the efficiency of the element decreases due to the light emission attenuation effect, so that in order to increase the color purity of the light emission and improve the light emitting efficiency, it is possible to use a host/dopant system including a light emitting material and a host or dopant material in the emission layer.

As a compound that may be used as a blue light emitting material of an organic EL device, for example, a polycyclic aromatic hydrocarbon such as a perylene-based compound, a pyrene-based compound, a chrysene-based compound, and an anthracene-based compound, a styrene-based hydrocarbon compound such as styrene or bisstyrylbenzene, aromatic amino group substituents thereof, and the like are known.

As an anthracene-based compound that may be used as a light emitting material, for example, 9,10-diaryl substituted anthracene is described in the specification of U.S. Pat. No. 5,935,721. This specification also describes a compound in which the aryl group is also substituted with a heteroaryl group, for example, a pyridyl group, and the like. In addition, International Publication No. WO 2005/056505 describes a compound in which a phenyl group with the ortho position being substituted with an aryl group is substituted at the 2-position of an anthracene ring, and the use of the compound as a light emitting material of an organic EL device. Furthermore, [Formula 7] to [Formula 11] of International publication No. 2005/113531 describe a compound in which a dibenzofuran or dibenzothiophene ring is bonded at the 4-position of an anthracene ring directly or via an arylene or heteroarylene group, and International publication No. 2005/113531 also describes the use of the compound as a light emitting material for an organic EL device. However, these patent documents do not describe a compound in which a dibenzofuran or dibenzothiophene ring is bonded to an anthracene ring at the 1-position of the dibenzofuran or dibenzothiophene ring directly or via an arylene or heteroarylene group, and the use of the compound as a light emitting material of an organic EL device.

DETAILED DESCRIPTION OF THE INVENTION

Technical Problem

As described above, various compounds have been developed as a material for an organic electronic device, for example, an organic EL device, for example, as a light emitting material, but there is still a need for developing a compound having excellent characteristics or a compound having a novel chemical structure which has not been known to date. The present invention has been made in an effort to provide a novel compound useful as a material for an organic electronic device, particularly, an organic EL device, particularly as a light emitting material, and an organic electronic device using the same, particularly, an organic EL device.

Technical Solution

To solve the problem, in the present invention, a compound described below is used as a material of an organic electronic device, particularly, a light emitting material of an organic EL device.

A compound of the present invention is represented by the following Formula 1:

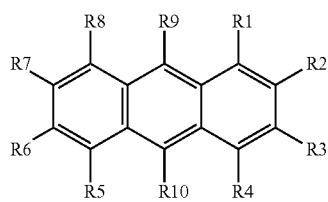

[Formula 1]

[In Formula 1, R1 to R10 are each independently selected from the group consisting of a hydrogen atom, a deuterium atom, a fluorine atom, a CN group, a substituted or unsubstituted alkyl group having 1 to 8 carbon atoms, a substituted or unsubstituted aryl group having 6 to 30 ring constituting carbon atoms, and a substituted or unsubstituted heteroaryl group having 5 to 30 ring substituting atoms; provided that at least one of R1 to R4 or R5 to R8 is represented by the following Formula 2:

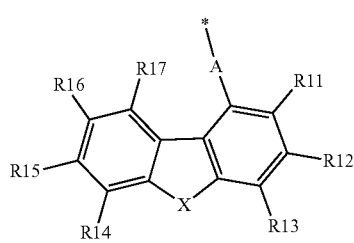

[Formula 2]

(In Formula 2, * denotes a binding site to the anthracene ring of Formula 1; A denotes a single bond, a substituted or unsubstituted arylene group having 6 to 30 ring constituting carbon atoms, or a substituted or unsubstituted heteroarylene group having 5 to 30 ring constituting atoms; X is an oxygen atom or a sulfur atom; and R11 to R17 are each independently selected from the group consisting of a hydrogen atom, a deuterium atom, a fluorine atom, a CN group, a substituted or unsubstituted alkyl group having 1 to 8 carbon atoms, a substituted or unsubstituted aryl group having 6 to 30 ring constituting carbon atoms, and a substituted or unsubstituted heteroaryl group having 5 to 30 ring constituting atoms.).].

Further, the compound of Formula 1 is preferably a compound represented by the following Formula 3:

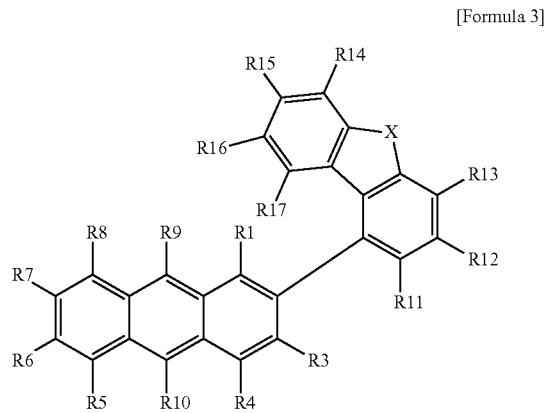

[Formula 3]

(In Formula 3, A, X, and R1 to R17 are the same as those defined above.).

In addition, the compound of Formula 1 is particularly preferably a compound represented by the following Formula 4:

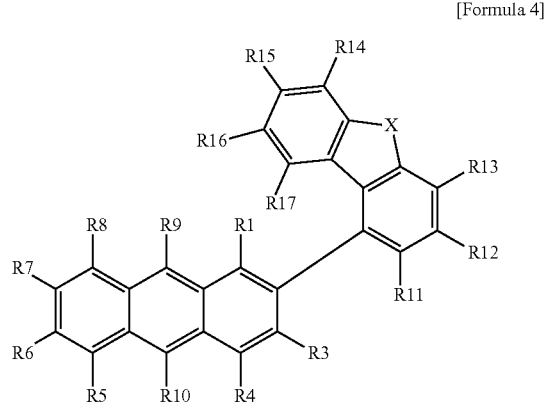

[Formula 4]

(In Formula 4, X and R1 to R17 are the same as those defined above).

In Formulae 1, 3, and 4, R9 and R10 are the same as or different from each other, and are each preferably a substituted or unsubstituted aryl group having 6 to 30 ring constituting carbon atoms.

In Formulae 1, 3, and 4, when R9 and/or R10 are/is a substituted aryl group, the substituent is preferably selected from the group consisting of a substituted or unsubstituted aryl group having 6 to 30 ring constituting carbon atoms and a substituted or unsubstituted heteroaryl group having 5 to 30 ring constituting atoms.

The compound of Formula 1 is particularly preferably a compound represented by the following Formula 5:

[Formula 5]

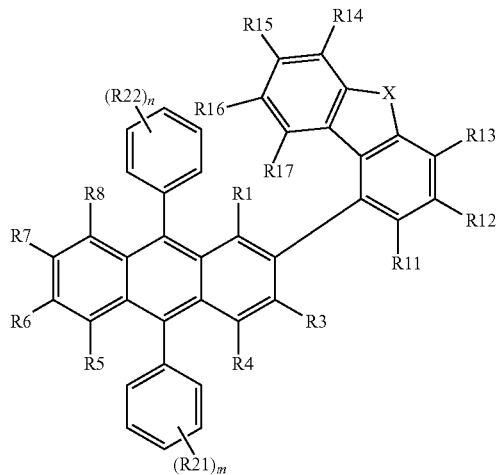

(In Formula 5, R1, R3, R4, R5 to R8, R11 to R17, and X are the same as those defined in Formula 1; R21 and R22 each independently denote a deuterium atom, an alkyl group having 1 to 8 carbon atoms, a substituted or unsubstituted aryl group having 6 to 30 ring constituting carbon atoms, and a substituted or unsubstituted heteroaryl group having 5 to 30 ring constituting atoms, and m and n each independently denote any one integer from 0 to 5.).

Among the compounds represented by Formula 5, particularly, a compound represented by the following Formula 6:

[Formula 6]

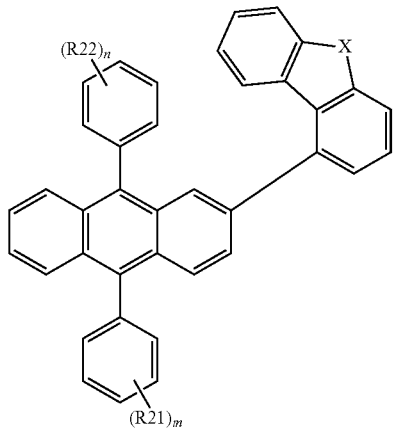

(In Formula 6, X is the same as that defined in Formula 1; R21 and R22 each independently denote a deuterium atom, an alkyl group having 1 to 8 carbon atoms, a substituted or unsubstituted aryl group having 6 to 30 ring constituting carbon atoms, and a substituted or unsubstituted heteroaryl group having 5 to 30 ring constituting atoms, and m and n each independently denote any one integer from 0 to 5.) is preferred.

The present invention also provides a material for an organic electronic device, consisting of the above-described compounds.

The organic electronic device is preferably an organic electroluminescence device (organic EL device).

The material for an organic electronic device is particularly preferably a light emitting material for an organic EL device.

The present invention also provides an organic EL device including any one of the above-described compounds particularly as a light emitting material.

Advantageous Effects

An organic electronic device using the compound according to an exemplary embodiment of the present application has an advantage of a long service life.

BRIEF DESCRIPTION OF DRAWINGS

The FIGURE is a view illustrating a typical structure of an organic EL device of the present invention.

EXPLANATION OF REFERENCE NUMERALS AND SYMBOLS

1: Substrate
2: Anode
3: Hole injection layer
4: Hole transport layer
5: Light emitting layer
6: Electron transport layer
7: Cathode

BEST MODE

The present invention will be described below in more detail.

In the present specification, the 'alkyl group' includes a straight-chained alkyl group, a branched alkyl group, and a cyclic alkyl group. Examples of a straight-chained or branched alkyl group having 1 to 8 carbon atoms include a methyl group, an ethyl group, an n-propyl group, an isopropyl group, an n-butyl group, an isobutyl group, a tert-butyl group, a pentyl group, a hexyl group, an octyl group, and a 2-ethylhexyl group, and the like, but are not limited thereto. Examples of the cyclic alkyl group include a cyclopropyl group, a cyclobutyl group, a cyclopentyl group, a cyclohexyl group, and an alkyl group including these cyclic alkyl partial structures, for example, a methylcyclopropyl group, a methylcyclohexyl group, and the like, but are not limited thereto.

In the present specification, the 'aryl group' refers to an aromatic hydrocarbon group, and examples thereof include a phenyl group, a biphenyl group, a terphenyl group, a fluorenyl group, a spirobifluorenyl group, a naphthyl group, an anthracenyl group, a phenanthryl group, an acenaphthylenyl group, a fluoranthenyl group, a pyrenyl group, a chrysenyl group, a triphenylenyl group, and a perylenyl group, but are not limited thereto. In the present specification, the fluorenyl group is also included in an aryl group or a substituted aryl group in a broad sense. In the present specification, the 'arylene group' refers to a divalent group in which one hydrogen atom is additionally removed from the 'aryl group'.

In the present specification, the 'heteroaryl group' refers to an aromatic heterocyclic group including one or more heteroatoms as a ring constituting atom, and examples thereof include an indenyl group, a benzoindenyl group, a pyrrolyl group, an indolyl group, a carbazolyl group, a furanyl group, a benzofuranyl group, a dibenzofuranyl group (particularly, a dibenzofuran-1-yl group, a dibenzofuran-2-yl group, a dibenzofuran-3-yl group, and a dibenzofuran-4-yl group), a thiophenyl group, a benzothiophenyl group, a dibenzothiophenyl group (particularly, a dibenzothiophene-1-yl group, a dibenzothiophene-2-yl group, a dibenzothiophene-3-yl group, and a dibenzothiophene-4-yl group), a selenophenyl group, a benzoselenophenyl group, a dibenzoselenophenyl group (particularly, dibenzoselenophene-1-yl, dibenzoselenophene-2-yl, a dibenzoselenophene-3-yl group, and a dibenzoselenophene-4-yl group), an imidazolyl group, a benzoimidazolyl group, a triazolyl group, an oxazolyl group, an oxadiazolyl group, a thiazolyl group, a thiadiazolyl group, a pyridyl group, a pyrimidyl group, a triazinyl group, a quinolinyl group, and a quinoxalinyl group, but are not limited thereto. In the present specification, the 'heteroarylene group' refers to a divalent group in which one hydrogen atom is additionally removed from the 'heteroaryl group'.

In the compound of the present invention, the above-described alkyl, aryl, heteroaryl, arylene, and heteroarylene groups may be each independently unsubstituted or have a substituent. The types of these substituents are not particularly limited, but are preferably a group independently selected from the group consisting of a deuterium atom, a halogen atom (for example, a fluorine atom, a chlorine atom, or a bromine atom), a cyano group, a nitro group, a straight-chained or branched alkyl group having 1 to 6 carbon atoms, a cycloalkyl group having 3 to 6 carbon atoms, an alkoxy group having 1 to 6 carbon atoms, an aryl group having 6 to 30 ring carbon atoms or a heteroaryl group having 5 to 30 ring atoms, an aryl group having 6 to 30 ring carbon atoms or a heteroaryloxy group having 5 to 30 ring atoms, a mono- or di-substituted amino group having an aryl group having 6 to 30 ring carbon atoms or a heteroaryl group having 5 to 30 ring atoms as a substituent, and a triarylsilyl or triheteroarylsilyl group having an aryl group having 6 to 30 ring carbon atoms or a heteroaryl group having 5 to 30 ring atoms as a substituent. The number of substituents, if any, may be any number from 1 to the maximum number that can be substituted.

Particularly preferred substituents are each independently selected from the group consisting of a deuterium atom, an aryl group having 6 to 30 ring carbon atoms, a heteroaryl group having 5 to 30 ring atoms, a monoarylamino group or a diarylamino group (the aryl group is an aryl group having 6 to 30 ring carbon atoms), and a triarylsilyl group (the aryl group is an aryl group having 6 to 30 ring carbon atoms).

The compound of the present invention is represented by the following Formula 1:

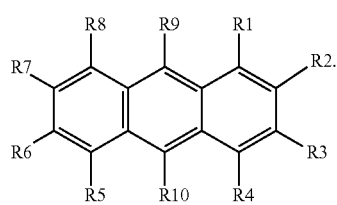

[Formula 1]

In Formula 1, R1 to R10 each independently denote a group selected from the group consisting of a hydrogen atom, a deuterium atom, a fluorine atom, a CN group, a substituted or unsubstituted alkyl group having 1 to 8 carbon atoms, a substituted or unsubstituted aryl group having 6 to 30 ring constituting carbon atoms, and a substituted or unsubstituted heteroaryl group having 5 to 30 ring constituting atoms.

However, Formula 1 is under a condition that at least one of R1 to R4 or R5 to R8, preferably any one or two of R2, R3, R6, or R7, more preferably, one of R2, R3, R6, or R7, or R2 and R6, R3 and R7, R2 and R7, or R3 and R6 are independently a group represented by the following Formula 2:

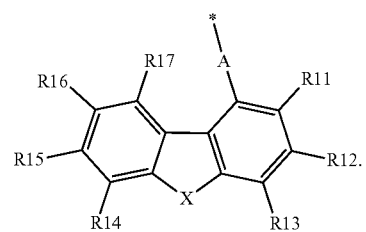

[Formula 2]

When two or more of R2, R3, R6, or R7 are a group represented by Formula 2, they are preferably the same group.

In Formula 2, * denotes a binding site to the anthracene ring of Formula 1; A denotes a single bond, a substituted or unsubstituted arylene group having 6 to 30 ring constituting carbon atoms, or a substituted or unsubstituted heteroarylene group having 5 to 30 ring constituting atoms, preferably a single bond or an unsubstituted arylene group, particularly preferably a single bond; X is an oxygen atom or a sulfur atom, preferably an oxygen atom; R11 to R17 are each independently selected from the group consisting of a hydrogen atom, a deuterium atom, a fluorine atom, a CN group, a substituted or unsubstituted alkyl group having 1 to 8 carbon atoms, a substituted or unsubstituted aryl group having 6 to 30 ring constituting carbon atoms, and a substituted or unsubstituted heteroaryl group having 5 to 30 ring constituting atoms. R11 to R17 are particularly preferably independently hydrogen or deuterium. The arylene group which A denotes is preferably independently a phenylene group, a biphenylene group, or a naphthylene group.

In the definition of Formula 1, alkyl, aryl, heteroaryl, arylene, heteroarylene, and substituents which they may have are the same as those described above.

The compound represented by Formula 1 is preferably a compound in which the group represented by Formula 2 is bonded at the 1-position or 9-position to the 2-, 3-, 6-, or 7-position of an anthracene ring represented by the following Formula 3:

[Formula 3]

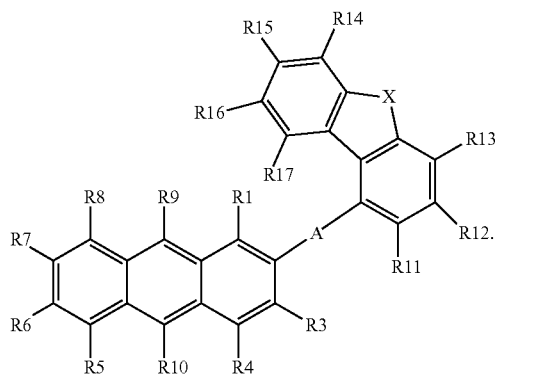

In Formula 3, A, X, and R1 to R17 are the same as those defined in Formulae 1 and 2 above.

Further, the compound of Formula 1 is preferably a compound represented by the following Formula 4:

[Formula 4]

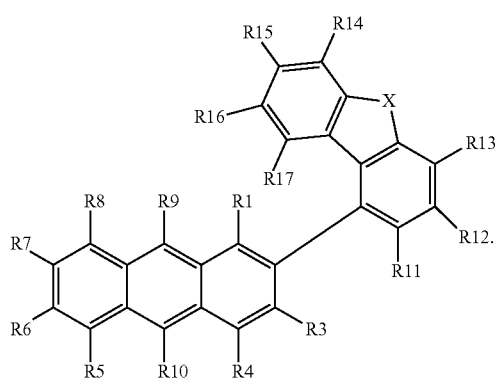

The compound of Formula 4 is the case where A in Formula 3 is a single bond.

In Formula 4, X and R1 to R17 are the same as those defined in Formulae 1 and 2.

Further, in Formulae 1, 3, and 4, R9 and R10 are the same as or different from each other, and are each preferably a substituted or unsubstituted aryl group having 6 to 30 ring constituting carbon atoms. The substituted or unsubstituted aryl group which R9 and R10 denote is preferably a group independently selected from the group consisting of phenyl, tolyl, dimethylphenyl, tert-butylphenyl, biphenyl, terphenyl, 1- or 2-naphthyl, and phenanthrenyl.

In addition, in Formulae 1, 3, and 4, when R9 and/or R10 are/is a substituted aryl group, the substituent is preferably a group selected from the group consisting of a substituted or unsubstituted aryl group having 6 to 30 ring constituting carbon atoms and a substituted or unsubstituted heteroaryl group having 5 to 30 ring constituting atoms. The substituents which aryl and heteroaryl groups may have are the same as those mentioned above.

Furthermore, in Formulae 1, 3, and 4, R9 and R10 are the same as or different from each other, are preferably the same as each other, and are each a substituted or unsubstituted aryl group having 6 to 30 ring constituting carbon atoms, and also, it is preferred that R1, R3, R4, R5, R6, R7, and R8 are independently a hydrogen or deuterium atom, preferably a hydrogen atom. The substituent which the aryl group having 6 to 30 ring constituting carbon atoms may have is the same as that described above, but is particularly preferably unsubstituted.

Even among the compounds of Formula 1, particularly preferable compound is a compound represented by the following Formula 5:

[Formula 5]

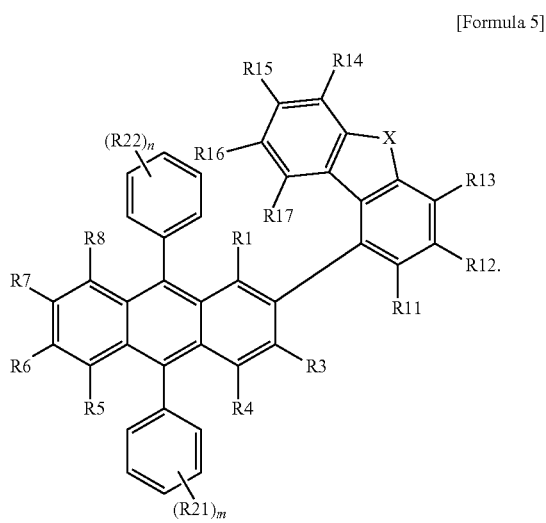

In Formula 5, R1, R3, R4, R5 to R8, R11 to R17, and X are the same as those defined in Formula 1; R21 and R22 each independently denote a deuterium atom, an alkyl group having 1 to 8 carbon atoms, a substituted or unsubstituted aryl group having 6 to 30 ring constituting carbon atoms, and a substituted or unsubstituted heteroaryl group having 5 to 30 ring constituting atoms, and particularly preferably each independently denote a deuterium atom, an alkyl group having 1 to 8 carbon atoms, or an unsubstituted aryl group having 6 to 30 ring constituting carbon atoms, and m and n each independently denote any one integer from 0 to 5, preferably 0 or 1, and particularly preferably 0. X is preferably an oxygen atom.

Among the compounds represented by Formula 5, particularly, a compound represented by the following Formula 6:

[Formula 6]

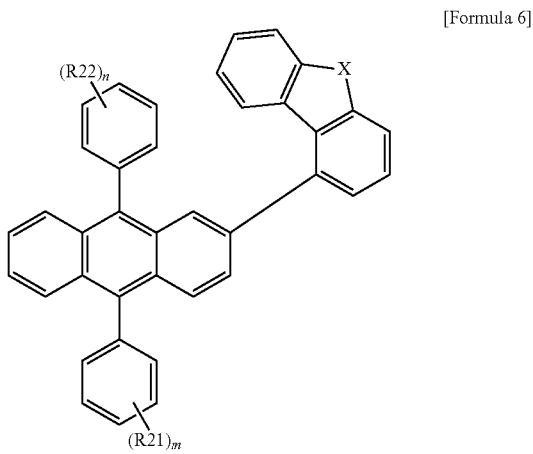

is preferred.

In Formula 6, X, R21, R22, m, and n are the same as those defined in Formula 5. X is preferably an oxygen atom. R21 and R22 are preferably independently an alkyl group having 1 to 8 carbon atoms, or an unsubstituted aryl group having 6 to 30 ring constituting carbon atoms.

Specific examples of the compound of the present invention will be shown below, but the compound of the present invention is not limited thereto.

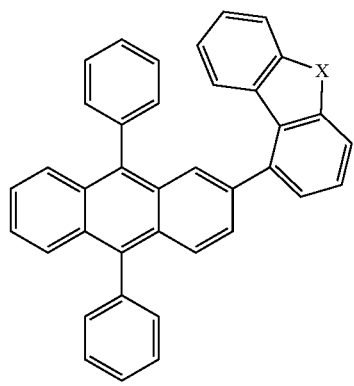

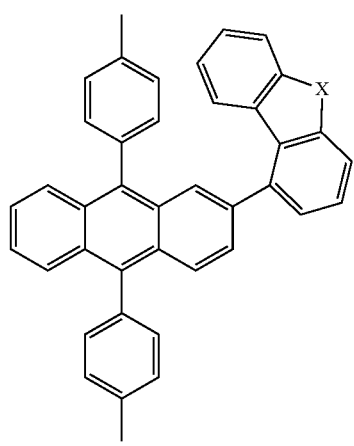

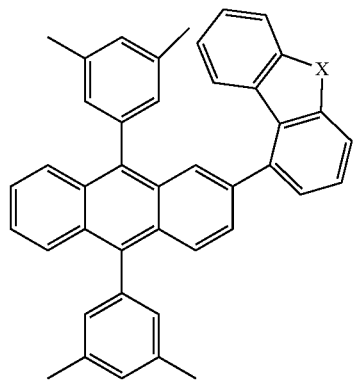

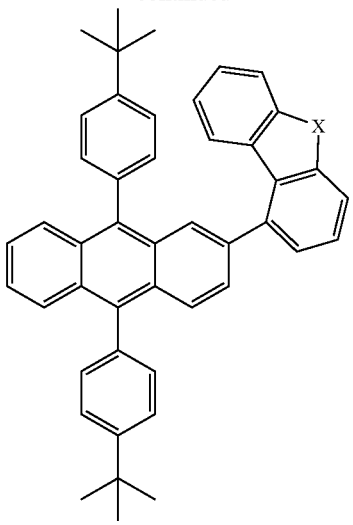

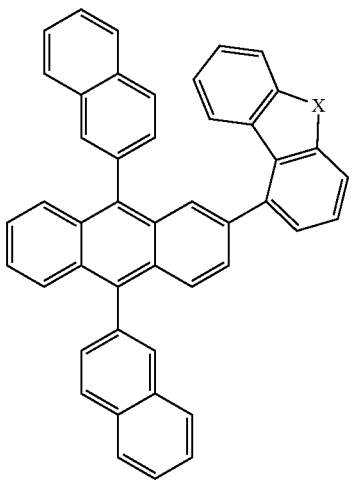

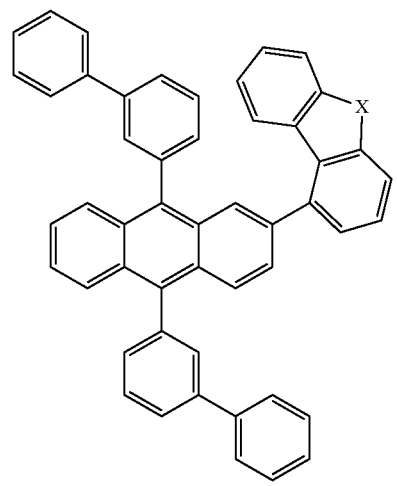

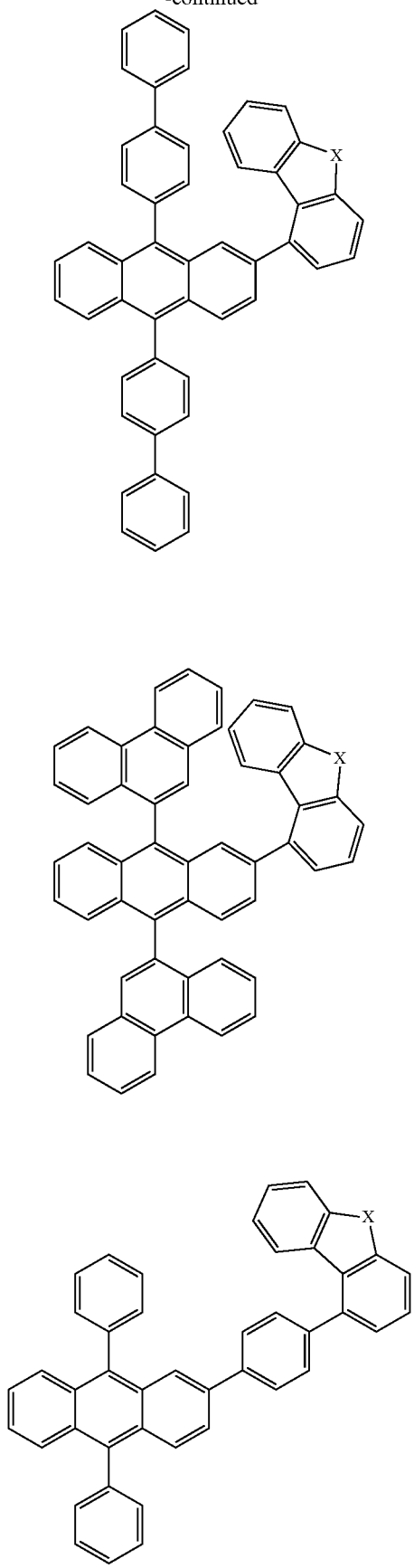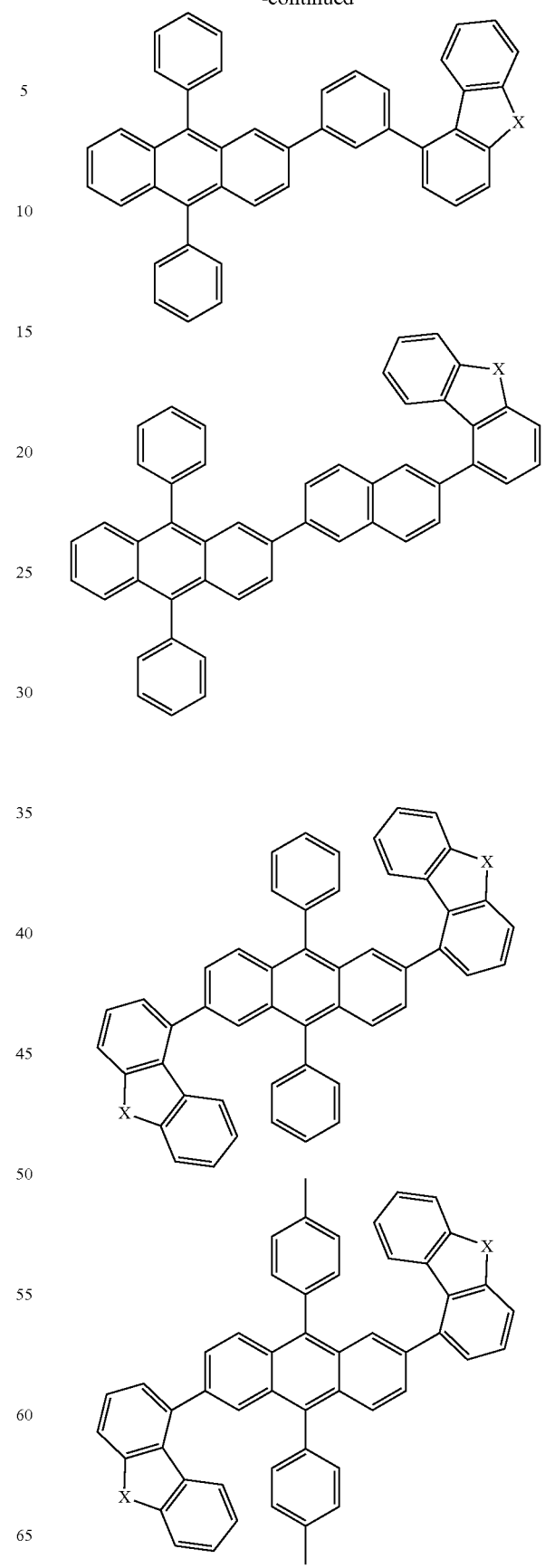

-continued

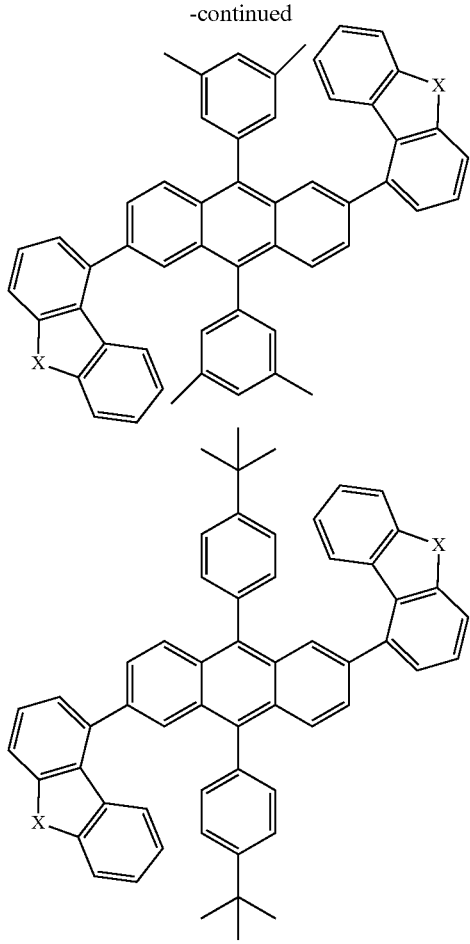

(In these formulae, X denotes O or S.)

It is possible to exhibit an effect in which an organic EL device having excellent characteristics is obtained by the fact that the compound of the present invention has an anthracene ring and a dibenzofuran-1-yl or dibenzothiophene-1-yl group (or a dibenzofuran-9-yl or dibenzothiophene-9-yl group) in the molecule and a dibenzofuran or dibenzothiophene ring is bonded at the 1-position (or 9-position) thereof, when the compound of the present invention is used as a light emitting material in comparison with an isomer in which a dibenzofuran or dibenzothiophene ring is bonded at a different position such as the 4-position thereof.

Therefore, the above-described compound of the present invention may be used as a material for an organic electronic device, particularly, a material for an organic EL device, particularly, a light emitting material for an organic EL device, preferably, as a blue light emitting material.

Therefore, the present invention also relates to an organic EL device including the compound of the present invention.

[Organic Electroluminescence Device (Organic EL Device)]

An organic EL device generally includes a first electrode, a second electrode, and one or more organic materials disposed therebetween, and at least one of the first electrode and the second electrode is a light transmissive electrode. When holes are injected from an anode into an organic layer and electrons are injected from a cathode into the organic layer by applying a voltage between these two electrodes, the holes and the electrons recombined in the organic material layer, and a light emitting body, that is, a light emitting material included in the organic material layer emits light using the energy of excitons generated by the recombination. The organic EL device has a structure in which light is emitted from the organic material layer thereof and light is extracted from the side of the light transmissive electrode. The device structure of the organic EL device is not limited to any one, and various device structures have been proposed. As for the light emitting method, a top emission type, a bottom emission type, a double emission (double light emitting) type, and the like are known. The organic material layer of the organic EL device of the present invention may have a single layer structure consisting of one layer or a multi-layer structure having two or more layers, including an emission layer. When the organic material layer of the organic EL device of the present invention has a multi-layer structure, the organic material layer may have, for example, a structure in which a hole injection layer, a hole transport layer, an emission layer, an electron transport layer, and the like are stacked. Further, it is known that characteristics of an organic EL device may be improved by providing various layers such as a planarization layer for enhancing the smoothness of the surface of an electrode, a hole blocking layer, an electron blocking layer, and/or an exciton blocking layer. The above-described compound of the present invention may be used in organic EL devices of all light emitting methods and structures. Therefore, the method of light emission and the device structure of the organic EL device including the compound of the present invention are not limited to specific ones. Further, the compound of the present invention is useful as a light emitting material for an organic EL device, particularly, a blue light emitting material.

A typical structure of the organic EL device is illustrated in the FIGURE. In the FIGURE, 1 denotes a substrate, 2 denotes an anode, 3 denotes a hole injection layer, 4 denotes a hole transport layer, 5 denotes an organic emission layer, 6 denotes an electron transport layer, and 7 denotes a cathode. Typically, an organic EL device having the structure illustrated as the FIGURE is called an organic EL device having a forward structure.

The organic EL device of the present invention may have the forward structure, but is not limited to this structure, and may be an organic EL device having a reverse structure, that is, a structure in which a substrate, a cathode, an electron transport layer, an organic emission layer, a hole transport layer, a hole injection layer, and a positive electrode are sequentially stacked. Furthermore, several of the plurality of organic layers may be omitted. Further, the organic EL device of the present invention is not limited to the above-described device structure, and may have any publicly known device structure as the structure of the organic EL device.

The organic EL device according to the present invention may be manufactured using methods for manufacturing an organic EL device and materials used for the organic EL device, which are publicly known, except for using the inclusion of the compound of the present invention in the organic layer as a condition. For example, the organic EL device according to the present invention may be manufactured by depositing a metal, an alloy, or a metal oxide having conductivity, or a combination thereof on a substrate to form an anode, forming an organic material layer including one or more layers including an emission layer selected from a hole injection layer, a hole transport layer, an emission layer, an electron transport layer, and the like thereon, and then depositing a material, which may be used as a cathode, thereon, by using a physical vapor deposition (PVD) method such as sputtering or e-beam deposition. In addition to the method, as described above, an organic EL device may be made by sequentially depositing a cathode material, an organic material layer, and an anode material on a substrate in order to manufacture the organic EL device having a reverse structure. Further, several of the above-described organic layers may be omitted, and organic layers other than those described above may be added.

As a method of forming an organic material layer, it is possible to use a solution method, for example, a method such as spin coating, dip coating, doctor blade coating, screen printing, inkjet printing, or a thermal transfer method, in addition to the vapor deposition method. In addition, a combination of solution and evaporation methods may be used for different organic layers in the organic EL device.

As a material for an anode, typically, it is preferred to use materials having a high work function so as to facilitate the injection of holes into an organic material layer. Specific examples of the anode material used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or $SnO_2$:Sb; a conductive polymer such as poly(3-methylthiophene), poly[3,4-(ethylene-1,2-dioxy) thiophene](PEDOT), polypyrrole, and polyaniline; and the like, but are not limited thereto.

As a material for a cathode, typically, it is preferred to use materials having a low work function so as to facilitate the injection of electrons into an organic material layer. Specific examples of the cathode material include: a metal such as magnesium, calcium, sodium, potassium, titanium, indium, yttrium, lithium, gadolinium, aluminum, silver, tin, and lead, or an alloy thereof; a multi-layer structured material, such as LiF/Al or $LiO_2$/Al, but are not limited thereto.

A hole injection material is a material that can smoothly receive the injection of holes from the anode at a low voltage, and it is preferred that the highest occupied molecular orbital (HOMO) of the hole injection material is between a work function of the anode material and the HOMO of the organic material layer opposite to the anode adjacent to the hole injection layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone and polyaniline, polythiophene-based conductive polymers and the like, but are not limited thereto.

The material of the hole transport layer is a material that can receive the transport of holes from the anode or the hole injection layer to move the holes to the emission layer, and a material having high hole mobility is suitable. Specific examples thereof include: arylamine-based compounds; carbazole-based compounds; anthracene-based compounds; pyrene-based compounds; conductive polymers, and block copolymers having both conjugated portions and non-conjugated portions, and the like, but are not limited thereto.

As the light emitting material constituting the emission layer, the compound of the present invention may be used. The emission layer may be constituted using the compound of the present invention alone, but it is preferred to form the emission layer by using the compound of the present invention as a light emitting host material and combining the compound of the present invention with a dopant material. When the compound of the present invention is used in combination with a dopant material, the amount of dopant material is preferably 0.01 to 50 mass %, and more preferably 1 to 20 mass % based on the mass of the compound of the present invention. As the host material of the emission layer, one or a combination of two or more of the compounds of the present invention may be used. Further, a light emitting body other than the compound of the present invention may be used in combination with the compound of the present invention.

Examples of the compound that may be used in combination with the compound of the present invention as the host material of the emission layer include compounds selected from non-polymer compounds such as fused ring derivatives such as anthracene or pyrene which is a light emitting body, aromatic amine derivatives such as N,N'-dinaphthyl-N,N'-diphenyl-4,4'-diphenyl-1,1'-diamine and 4,4'-bis[4-di-p-tolylamino]styryl]biphenyl, metal chelated oxynoid compounds such as tris(8-quinolinato)aluminum (III), bisstryl derivatives such as distyrylbenzene derivatives, tetraphenylbutadiene derivatives, indene derivatives, coumarin derivatives, oxadiazole derivatives, pyrrolopyridine derivatives, perinone derivatives, cyclopentadiene derivatives, oxadiazole derivatives, carbazole derivatives, and pyrrolopyrrole derivatives; and polymer compounds such as polyphenylenevinylene derivatives, polyparaphenylene derivatives, polyfluorene derivatives, polyvinylcarbazole derivatives, and polythiophene derivatives, but are not limited to these compounds.

Meanwhile, in the emission layer, when the compounds of the present inventions are used either alone or in combination with two or more thereof as a host material, examples of the compound that may be used in combination with the host material as a dopant material include compounds having an aryl ring such as naphthalene, anthracene, phenanthrene, pyrene, triphenylene, perylene, fluorene, and indene or derivatives thereof, for example, 2-(benzothiazole-2-yl)-9,10-diphenylanthracene or 5,6,11,12-tetraphenylnaphthacene; compounds having heteroaryl rings such as furan, pyrrole, thiophene, silole, 9-silafluorene, 9,9'-spirobisilafluorene, benzothiophene, benzofuran, indole, dibenzothiophene, dibenzofuran, imidazopyridine, phenanthroline, pyrazine, naphthyridine, quinoxaline, pyrrolopyridine, and thioxanthene or derivatives thereof; distyrylbenzene derivatives, and aminostyryl derivatives such as 4,4'-bis(2-(4-diphenylaminophenyl)ethenyl)biphenyl, 4,4'-bis[4-di-p-tolylamino]styryl]biphenyl, and 4,4'-bis(N-(stilben-4-yl)-N-phenylamino)stilbene; aromatic acetylene derivatives, tetraphenylbutadiene derivatives, stilbene derivatives, aldazine derivatives, pyrromethene derivatives, diketopyrrolo[3,4-c]pyrrole derivatives, and coumarin derivatives such as 2,3,5,6-1H,4H-tetrahydro-9-(2'-benzothiazolyl)quinolizino[9,9a,1-gh]coumarin; azole derivatives such as imidazole, thiazole, thiadiazole, carbazole, oxazole, oxadiazole, and triazole and metal complexes thereof; and aromatic amine derivatives such as N,N'-diphenyl-N,N'-di(3-methylphenyl)-4,4'-diphenyl-1,1'-diamine, and the like. Further, the aromatic amino group-containing heterocyclic compounds described in International Publication No. WO 2015/174682 may also be included as a preferred compound that may be used as a dopant material when the compound of the present invention is used as a host material of the emission layer. However, the compounds that may be used as a dopant material are not limited thereto.

An electron transport material is a material that can smoothly receive the injection of electrons from the cathode to move the electrons to the emission layer, and it is preferred to use a material having high electron mobility. Specific examples of the electron transport material include Al complexes such as 8-hydroxyquinoline; complexes including Alq$_3$; organic radical compounds; hydroxyflavone-metal complexes; anthracene-based compounds; pyrene-based compounds; benzoxazole-based, benzothiazole-based, and benzoimidazole-based compounds; pyridine-based compounds; phenanthroline-based compounds; quinoline-based compounds; quinazoline-based compounds, and the like, but are not limited thereto. In addition, an electron transport layer may be formed by doping these compounds with a metal or metal compound.

In addition to the above-described respective layers, a planarization layer for enhancing the smoothness of the surface of an electrode; and a layer selected from a hole blocking layer, an electron blocking layer, and an exciton blocking layer for confining holes, electrons, and/or excitons in a target organic layer may be used in the organic EL device, if necessary, and such as technology is a publicly known technology. In addition, the publicly known technology for the organic EL device may be applied to an organic EL device including the compound of the present invention.

The compound of the present invention is not limited to the above-described organic EL device, and may be used as a material for other organic electronic devices, for example, a device such as an organic solar cell, an organic photo conductor, an organic photo sensor, and an organic transistor. The operation principles of these devices and the device structures are known in the art. Hereinafter, the results of the Comparative Examples and the preferred Examples will be provided for helping the understanding of the present invention, and the present invention is not limited to the following Examples.

MODE FOR INVENTION

Examples

Synthesis Examples (1) Synthesis of Compound A

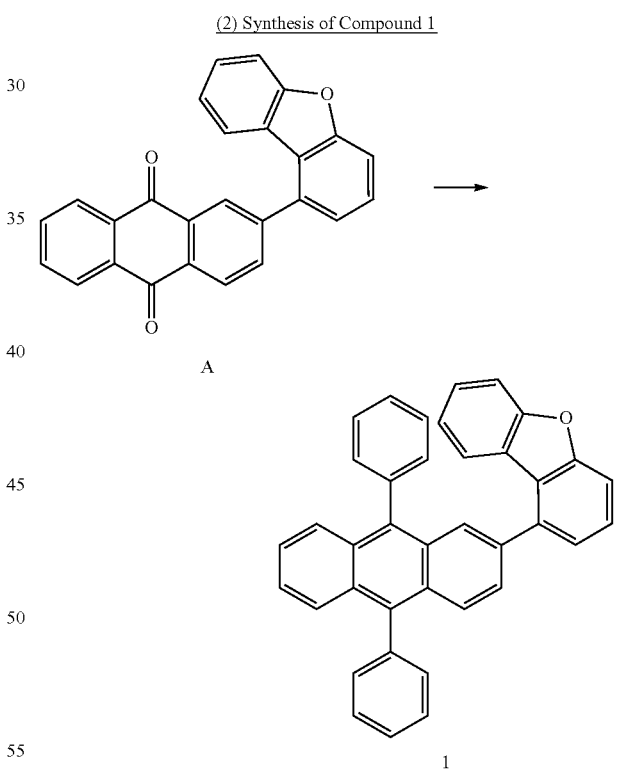

2-iodoanthraquinone (Mw 334.1, 4.68 g, 14 mmol), dibenzofuran-1-boronic acid (Mw 212.01, 3.6 g, 17 mmol), 0.32 g (0.35 mmol) of tris(dibenzylideneacetone)dipalladium(0), 14 g (43 mmol) of cesium carbonate, and 40 ml of anhydrous dioxane were put into a 300 ml three-neck flask equipped with an argon inlet and a stirring device under an argon atmosphere, and the resulting mixture was stirred and prepared as a suspension. 1.1 ml (0.98 mmol) of a tricyclohexylphosphine solution at a concentration of 25 mass % in toluene was added to the suspension, and the obtained mixture was heated and stirred for reaction at 80° C. under an argon atmosphere for 10 hours. After the reaction, about 100 ml of water and about 300 ml of toluene were added to the reaction suspension and the suspension was stirred, and then the mixture was filtered through Celite (manufactured by Wako Pure Chemical Industries, Ltd, Catalogue No. 531-16855). The obtained filtrate was washed with 50 ml of saturated saline, and water was absorbed by adding magnesium sulfate to the organic layer. The suspension was further filtered through Celite, and the obtained filtrate was concentrated. Methanol was added to the concentrate, and the mixture was irradiated with ultrasonic waves. 4.7 g of a light yellow powder was obtained at a yield of 91% by collecting the resulting solid by filtration and drying the collected solid. This is designated as Compound A (field desorption mass analysis; m/z=374 was observed).

(2) Synthesis of Compound 1

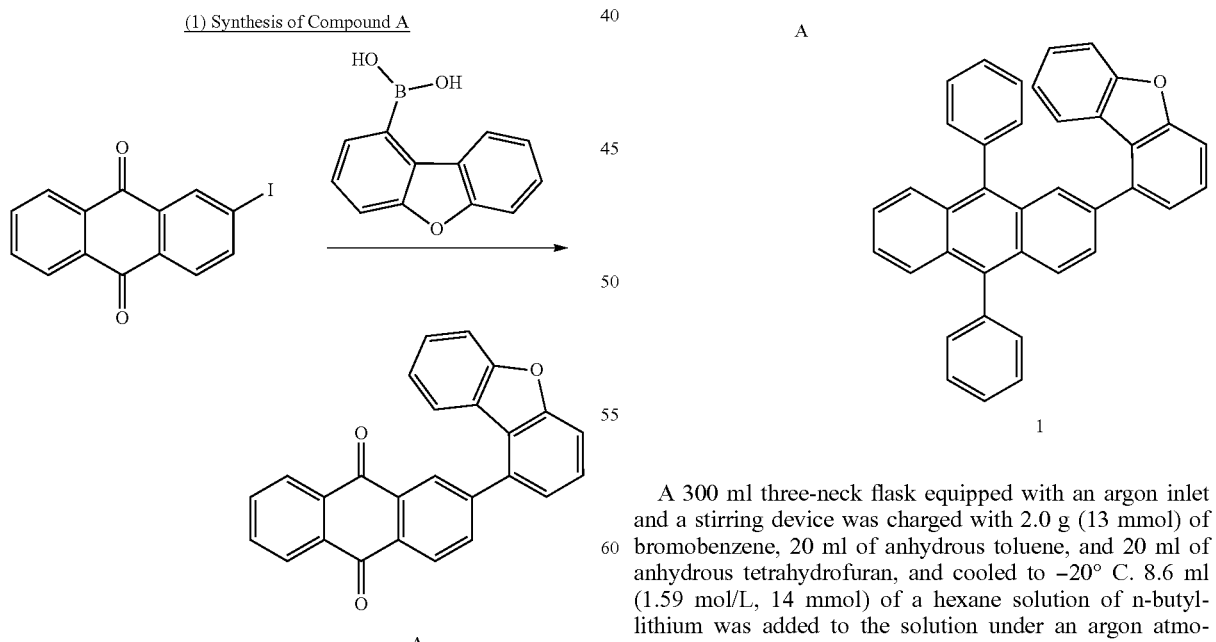

A 300 ml three-neck flask equipped with an argon inlet and a stirring device was charged with 2.0 g (13 mmol) of bromobenzene, 20 ml of anhydrous toluene, and 20 ml of anhydrous tetrahydrofuran, and cooled to −20° C. 8.6 ml (1.59 mol/L, 14 mmol) of a hexane solution of n-butyllithium was added to the solution under an argon atmosphere, and the resulting solution was stirred at −20° C. for 1 hour. Next, 1.5 g of Compound A was added thereto, and the resulting mixture was stirred at room temperature for 5 hours. Next, 50 ml of a saturated aqueous NH$_4$Cl solution was added thereto, and the organic layer was separated, washed with 50 ml of saturated saline, dried over magnesium sulfate, and then concentrated. Next, vacuum deaeration was performed for 3 minutes until no bubbles appeared. 0.5 ml (0.3 mmol) of a 10 mass % hexane solution of tri-t-butylphosphine was added to the solution, and the mixture was heated and stirred for reaction at 120° C. under a nitrogen atmosphere for 5 hours. The resulting oil was purified with column chromatography to obtain 0.8 g of a white powder (yield 39%). The white powder was found to be Compound 1 (field desorption mass analysis; m/z=496 was observed).

Device Example 1

First, a surface treatment using UV-ozone ($O_3$) was performed on an ITO glass substrate with a pattern formed and cleaned in advance. The thickness of the ITO layer (first electrode) on the ITO glass substrates was about 150 nm. After the surface treatment, the glass substrate was put into a deposition device for forming an organic layer, and each one of a hole injection layer, a hole transport layer (HTL), an emission layer, and an electron transport layer was deposited at a vacuum degree of about 10-4 to about 10-6 Pa.

The hole injection layer was formed to have a layer thickness of about 60 nm using 4,4',4"-tris(N,N-2-naphthylamino)triphenylamine (2-TNATA). The hole transport layer (HTL) was formed to have a layer thickness of about 30 nm using N,N'-bis(naphthyl-1-yl)-N,N'-diphenyl-4,4'-benzidine (NPD). The emission layer was formed to have a layer thickness of about 25 nm using Compound 1 as a light emitting host material and Compound D-1 shown below as a dopant material. The doping amount of the dopant material was 5 mass % based on the total amount of the host material. The electron transport layer was formed to have a layer thickness of 25 nm using $Alq_3$.

Next, the substrate was transferred to a deposition device for forming a metal layer, and the electron injection layer and the second electrode were deposited at a vacuum degree of about 10-4 to about 10-6 Pa, thereby manufacturing an organic EL device.

The electron injection layer was formed to have a layer thickness of about 1 nm using lithium fluoride (LiF), and the second electrode was formed to have a layer thickness of about 100 nm using aluminum. Thus, an organic EL device of Example 1 was manufactured by the above-described method.

Comparative Example 1

An organic EL device of Comparative Example 1 was manufactured in the substantially same manner as the method described in Example 1, except that an emission layer (EML) was formed using Compound Ref-1 instead of Compound 1.

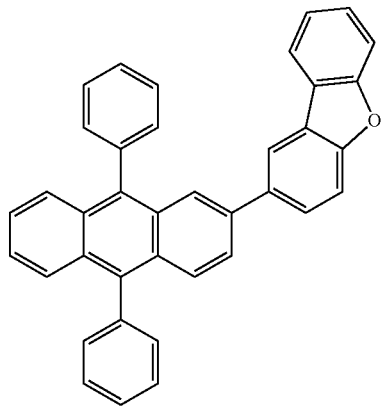

Ref-1

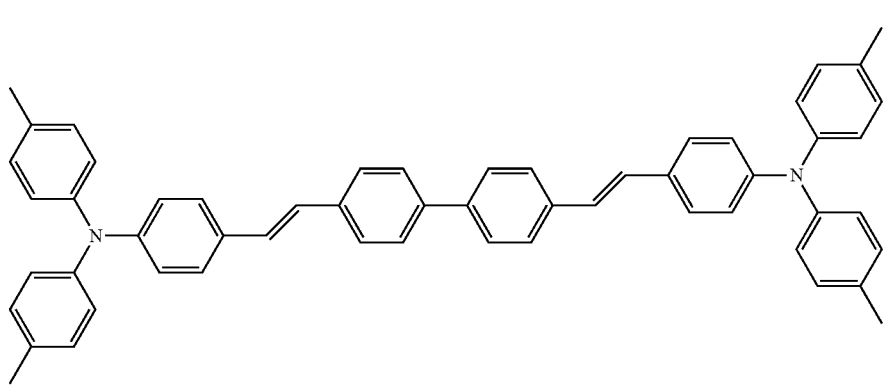

D-1

The evaluation results of each organic EL device manufactured according to Example 1 and Comparative Example 1 are shown in Table 1. The light emission characteristics of the manufactured organic EL device were evaluated at a current density of 10 mA/cm² using a C9920-11 brightness light distribution characteristics measurement system manufactured by Hamamatsu Photonics K.K. In Table 1, LT95 is a value indicating the time required to reach 95% of the initial brightness as a relative value.

TABLE 1

| | Host material of emission layer | Light emission color | LT95 (relative value) |
| --- | --- | --- | --- |
| Example 1 | Compound 1 | Blue | 1.0 |
| Comparative Example 1 | Ref-1 | Blue | 0.6 |

Referring to the result shown in Table 1, it can be seen that the service life of the organic EL device in Example 1, in which an emission layer (EML) is formed using Compound 1 according to an aspect of the present invention, is improved as compared to that of the organic EL device in Comparative Example 1, which is manufactured using Compound Ref-1 in which the bonding position of dibenzofuran for the anthracene ring is different from that of Compound 1.

INDUSTRIAL APPLICABILITY

The compound of the present invention can be used as a material for an organic electronic device, particularly, as a light emitting material for an organic EL device.

The invention claimed is:

1. An organic electroluminescence device comprising a light emitting layer comprising a host material and a dopant material,
   wherein the host material comprises a compound represented by Formula 1:

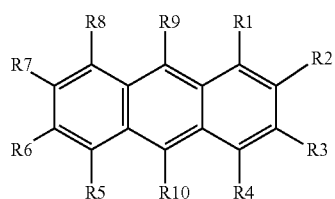

[Formula 1]

wherein, R1, R3-R5, R7 and R8 are each independently a hydrogen atom or a deuterium atom; R9 and R10 are each independently a phenyl or a naphthyl optionally substituted; and R2 and R6 are each independently a hydrogen atom, a deuterium atom or represented by Formula 2, provided that at least one of R2 or R6 is represented by Formula 2:

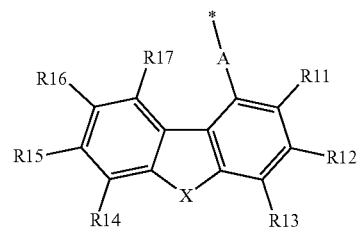

[Formula 2]

wherein, * denotes a binding site to the anthracene ring of Formula 1; A denotes a single bond; X is an oxygen atom or a sulfur atom; and R11 to R17 are each a hydrogen atom, or a deuterium atom, wherein the dopant material is a compound having an aryl ring selected from the group consisting of a naphthalene, phenanthrene, pyrene, triphenylene, perylene, fluorene and indene, provided that the dopant material does not comprise a compound comprising an anthracene group.

2. The organic electroluminescence device of claim 1, wherein the compound is represented by Formula 4:

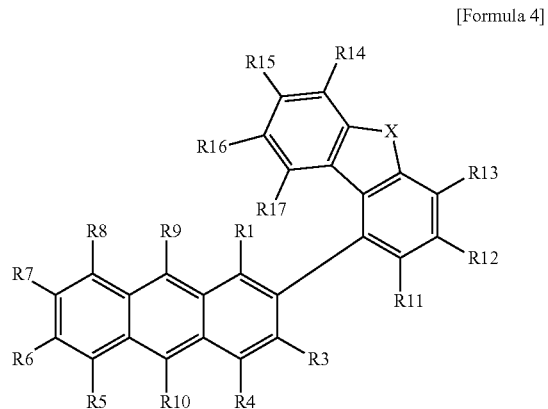

[Formula 4]

wherein, R6 is a hydrogen atom or a deuterium atom, X and R1 to R5 and R7 to R17 are the same as those defined in Formula 1.

3. The organic electroluminescence device of claim 1, wherein R9 and R10 are the same as or different from each other, and are each independently a substituted phenyl.

4. The organic electroluminescence device of claim 3, wherein R9 and R10 are the same as or different from each other, and are each independently a phenyl or a naphthyl substituted with a substituted or unsubstituted aryl group having 6 to 30 ring constituting carbon atoms or a substituted or unsubstituted heteroaryl group having 5 to 30 ring constituting atoms.

5. The organic electroluminescence device of claim 1, wherein the compound is represented by Formula 5:

[Formula 5]

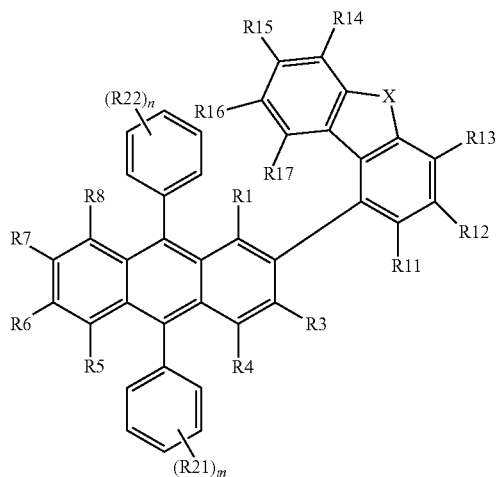

wherein, R1, R3 R4, R5 to R8, R11 to R17, and X are the same as those defined in Formula 1; R21 and R22 each independently denote a deuterium atom, an alkyl group having 1 to 8 carbon atoms, a substituted or unsubstituted aryl group having 6 to 30 ring constituting carbon atoms, or a substituted or unsubstituted heteroaryl group having 5 to 30 ring constituting atoms, and m and n each independently denote any one integer from 0 to 5.

6. The organic electroluminescence device of claim 5, wherein the compound is represented by Formula 6:

[Formula 6]

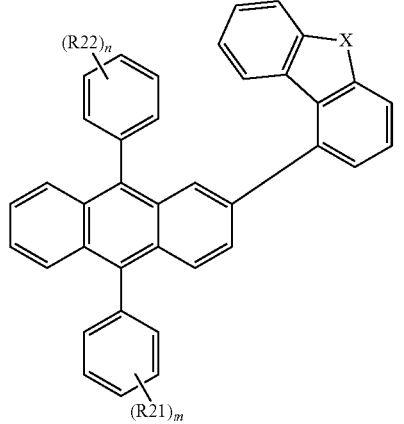

wherein, X is the same as that defined in Formula 5; R21 and R22 each independently denote a deuterium atom, an alkyl group having 1 to 8 carbon atoms, a substituted or unsubstituted aryl group having 6 to 30 ring constituting carbon atoms, or a substituted or unsubstituted heteroaryl group having 5 to 30 ring constituting atoms, and m and n each independently denote any one integer from 0 to 5.

7. The organic electroluminescence device of claim 1, wherein R6 is hydrogen or deuterium.

8. The organic electroluminescence device of claim 1, wherein R11 to R17 are each independently hydrogen.

9. The organic electroluminescence device of claim 1, wherein R9 and R10 are each independently selected from the group consisting of phenyl, tolyl, dimethylphenyl, tert-butylphenyl, biphenyl, terphenyl, and 1- or 2-naphthyl.

10. The organic electroluminescence device of claim 5, wherein m and n each independently an integer of 0 or 1.

11. The organic electroluminescence device of claim 1, wherein the compound is represented by any of the following formulas:

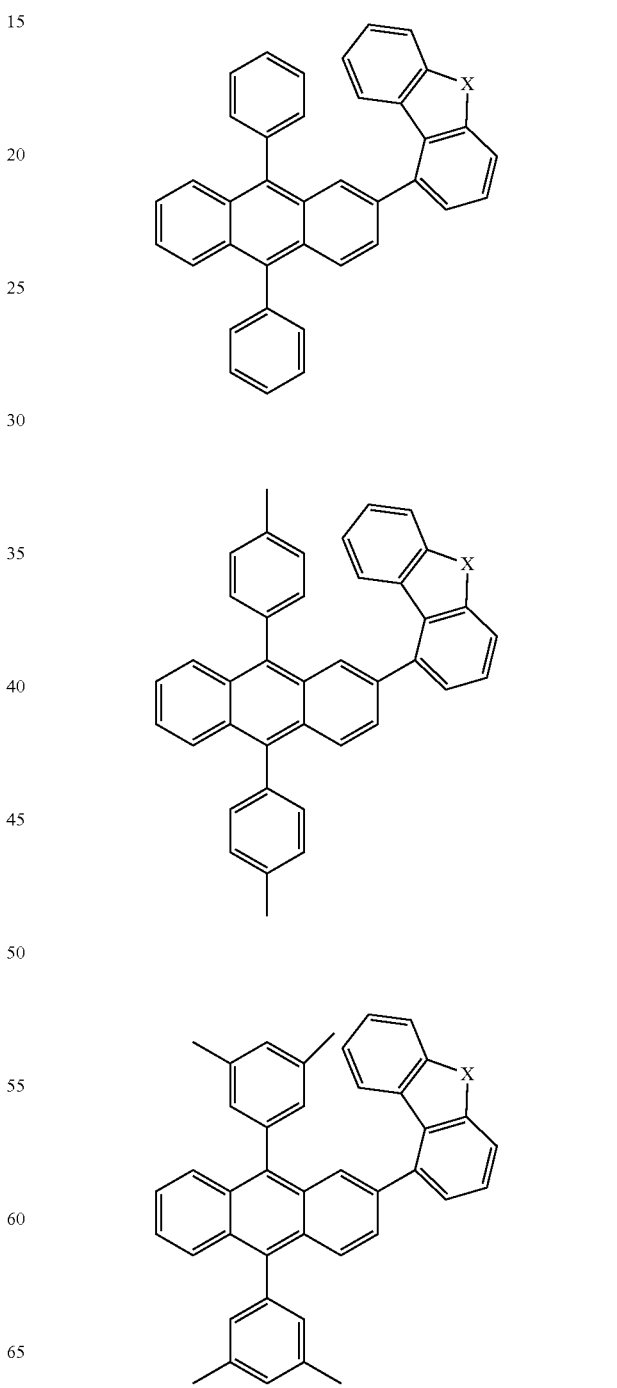

-continued
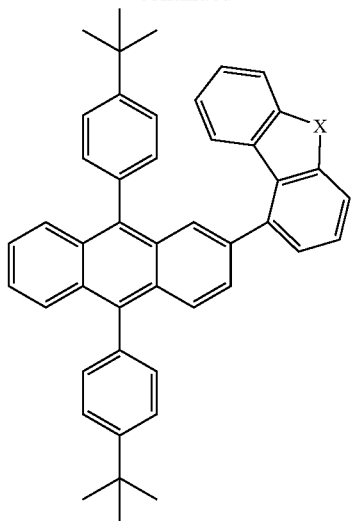
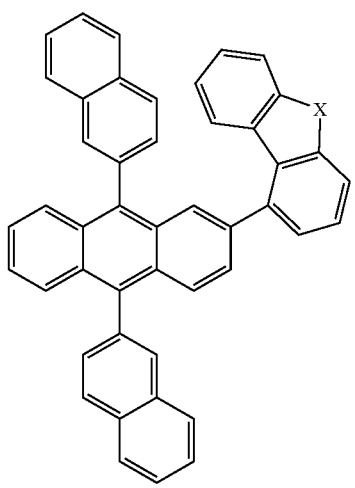
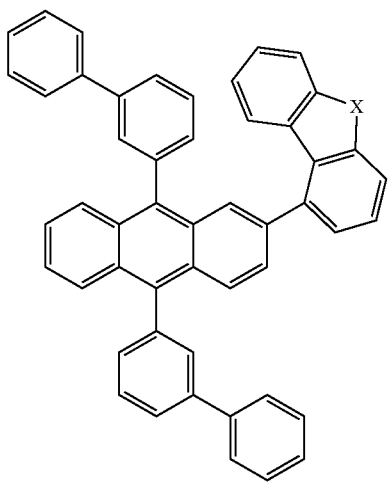
-continued
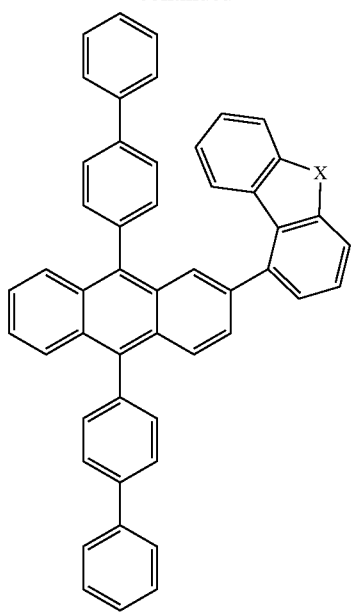
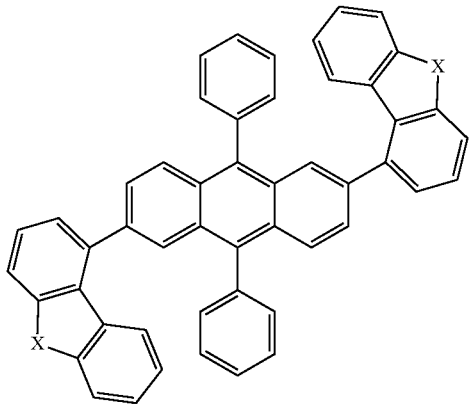
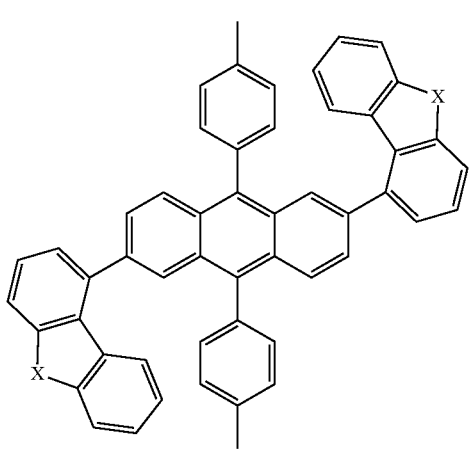

-continued
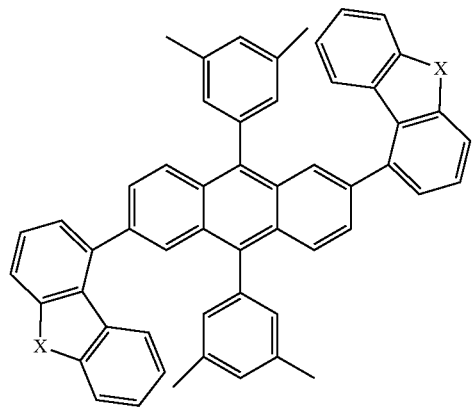
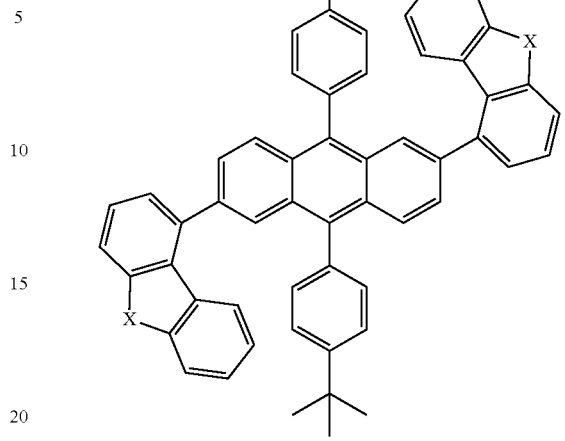
wherein X denotes O or S.
* * * * *